United States Patent
Nuijens et al.

(10) Patent No.: US 7,067,713 B2
(45) Date of Patent: Jun. 27, 2006

(54) C1 INHIBITOR PRODUCED IN THE MILK OF TRANSGENIC NON-HUMAN MAMMALS

(75) Inventors: Jan Henricus Nuijens, Heiloo (NL); Henricus Antonius Van Veen, Boskoop (NL); Frank Robert Pieper, Heemstede (NL); Joris Jan Heus, Amsterdam (NL)

(73) Assignee: Pharming Intellectual Property B.V., Leiden (NL)

( * ) Notice: Subject to any disclaimer, the term of this patent is extended or adjusted under 35 U.S.C. 154(b) by 375 days.

(21) Appl. No.: 10/181,704

(22) PCT Filed: Jan. 31, 2001

(86) PCT No.: PCT/NL01/00068

§ 371 (c)(1),
(2), (4) Date: Jul. 17, 2002

(87) PCT Pub. No.: WO01/57079

PCT Pub. Date: Aug. 9, 2001

(65) Prior Publication Data

US 2003/0140358 A1 Jul. 24, 2003

Related U.S. Application Data

(60) Provisional application No. 60/187,580, filed on Mar. 7, 2000, provisional application No. 60/179,310, filed on Jan. 31, 2000.

(30) Foreign Application Priority Data

Jan. 31, 2000 (EP) .................................. 00200320
Mar. 7, 2000 (EP) .................................. 00200810

(51) Int. Cl.
*C12P 21/00* (2006.01)
*A01K 67/27* (2006.01)

(52) U.S. Cl. .............................. 800/14; 800/7; 800/15; 800/16; 800/17; 800/18

(58) Field of Classification Search ............ 800/14–18, 800/7; 426/580; 514/12
See application file for complete search history.

(56) References Cited

U.S. PATENT DOCUMENTS 5,633,076 A * 5/1997 DeBoer et al. ............... 800/25

FOREIGN PATENT DOCUMENTS

| EP | 0586909 A | 3/1994 |
|----|-----------|--------|
| FR | 2601034 A | 1/1988 |
| WO | WO 9106650 A | 5/1991 |
| WO | WO 9222320 A | 12/1992 |
| WO | WO 9603051 A | 2/1996 |

OTHER PUBLICATIONS

Houdebine, L. M. Transgenic Animal Bioreactor. Transgenic Res. vol. 9, pp. 305-320.*
Koles, K. et al. Influence of Lactation Parameters on the N-Glycosylation of Recombinant Human C1 Inhibitor Isolated from the Milk of Transgenic Rabbits. Glycobiology. vol. 14, No. 11, pp. 979-986.*
Bork et al. :Long-Term Prophylaxis with C1-Inhibitor (C1 INH) Concentrate in Patients with Recurrent Angioedema Caused by Hereditary and Acquired C1-Inhibitor Deficiency. J. Allery Clinical Immunology. 1989, vol. 83, pp. 677-682.*
Carter P. et al., Euro J. Biochem. 173;163, 1988.
Cicardi, M. et al., Immunobiol. 199:366, 1998.
De Filippi, F et al., Transfusion 38:307, 1998.
Eldering, E. et al., J. Biol. Chem. 263:11776, 1988.
Hack, C. et al., LANCET, 339:8789 378, 1992.
Schapira, M. et al., 1985, Complement 2:111/Davis A.E., 1988, Ann. Rev. Immunol. 6:595.
Zurlo J. et al. Fertility and Sterility 54:64, 1990.

* cited by examiner

*Primary Examiner*—Deborah Crouch
(74) *Attorney, Agent, or Firm*—Townsend and Townsend and Crew, LLP

(57) ABSTRACT

The invention provides transgenic nonhuman mammals expressing C1 inhibitor in their milk. The C1 inhibitor is useful in treating patients with hereditary angioedema or patients requiring immunosuppression.

18 Claims, 2 Drawing Sheets

SEQUENCE LISTING

<160> NUMBER OF SEQ ID NOS: 10

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence: forward
      primer

<400> SEQUENCE: 1
tctctcagat cttccacagc c                                            21

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence:  reverse
      primer

<400> SEQUENCE: 2
aaggtcttca cctgctctgc                                              20

<210> SEQ ID NO 3
<211> LENGTH: 33
<212> TYPE: DNA
<213> ORGANISM: Artificial Sequence
<220> FEATURE:
<223> OTHER INFORMATION: Description of Artificial Sequence: linker-1
      sense

<400> SEQUENCE: 3
tcgacgaatt cggccccgg ggccgcggcc gca                                33

<210> SEQ ID NO 4
<211> LENGTH: 33
<212> TYPE: DNA
<213> ORGANISM: Artificial Sequence
<220> FEATURE:
<223> OTHER INFORMATION: Description of Artificial Sequence: linker-1
      anti-sense

<400> SEQUENCE: 4
aatttgcggc cgcggccccg ggggccgaat tcg                               33

```
<210> SEQ ID NO 5
<211> LENGTH: 54
<212> TYPE: DNA
<213> ORGANISM: Artificial Sequence
<220> FEATURE:
<223> OTHER INFORMATION: Description of Artificial Sequence: linker-2
      sense

<400> SEQUENCE: 5
ggccgcatcg atttgcttct ttccagtctt ggcccagatg gccccatgga cgcg            54

<210> SEQ ID NO 6
<211> LENGTH: 54
<212> TYPE: DNA
<213> ORGANISM: Artificial Sequence
<220> FEATURE:
<223> OTHER INFORMATION: Description of Artificial Sequence: linker-2
      anti-sense

<400> SEQUENCE: 6
tcgacgcgtc catggggcca tctgggccaa gactggaaag aagcaaatcg atgc            54

<210> SEQ ID NO 7
<211> LENGTH: 36
<212> TYPE: DNA
<213> ORGANISM: Artificial Sequence
<220> FEATURE:
<223> OTHER INFORMATION: Description of Artificial Sequence: linker-3
      sense

<400> SEQUENCE: 7
tggccgacgg ccaacatggc cgcggccgcg atatca                               36

<210> SEQ ID NO 8
<211> LENGTH: 42
<212> TYPE: DNA
<213> ORGANISM: Artificial Sequence
<220> FEATURE:
<223> OTHER INFORMATION: Description of Artificial Sequence: linker-3
      antisense

<400> SEQUENCE: 8
cgcgtgatat cgcggccgcg gccatgttgg ccgtcgccat ct                        42

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: linker-4
      sense

<400> SEQUENCE: 9
ctagtgcggc cgctgatcag                                                 20

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: linker-4
      anti-sense

<400> SEQUENCE: 10
tcgactgatc agcggccgca                                                 20
```

C1 INHIBITOR PRODUCED IN THE MILK OF TRANSGENIC NON-HUMAN MAMMALS

TECHNICAL FIELD

The present invention resides in the fields of recombinant genetics, and medicine, and is directed to transgenic production of C1 inhibitor and its use as a therapeutic molecule, e.g. in replacement therapy in patients with hereditary angioedema or patients requiring immunosuppression.

BACKGROUND OF THE INVENTION

Human C1 inhibitor, also known as C1 esterase inhibitor, is a well-known and identified substance. C1 inhibitor belongs to the superfamily of serine proteinase inhibitors and is the only inhibitor of C1r and C1s of the complement system and is the major inhibitor of factor XIIa and kallikrein of the contact system. In addition C1 inhibitor inhibits also other serine proteases of the coagulation and fibrinolytic systems like factor XI, tissue type plasminogen activator and plasmin (Schapira M. et al. 1985, Complement 2:111/Davis A. E. 1988, Ann. Rev. Immunol. 6:595).

C1 inhibitor is encoded by a single gene on chromosome 11 and consists of 8 exons and 7 introns. The entire genomic sequence is known and codes for a protein of 500 amino acids, including a 22 amino acid signal sequence (Carter P. et al. 1988, Euro. J. Biochem. 173; 163). Plasma C1 inhibitor is a glycoprotein of approximately 105 kDa and is heavily glycosylated, up to 50% of its molecular mass consists of carbohydrate.

Currently only C1 inhibitor obtained from human blood, either highly or partially purified, is used and approved in some European countries for the treatment of hereditary angioedema. This is a disease caused by a genetic deficiency of C1 inhibitor and characterized by attacks of well-circumscribed non-pitting subepithelial edema resulting from a local increase in vasopermeability (Cicardi M. et al 1998, Immunobiol. 199: 366). The three sites primarily involved are: subcutaneous tissue (extremities, face, genitals, buttocks), abdominal organs and the upper airway (larynx). Swelling of the intestinal mucous can be very painful and laryngeal edema is a life-threatening situation.

Prophylactic treatment using androgens or fibrinolytic agents is used to reduce the number and severity of attacks but they are not efficient against acute crises and besides, they induce side effects that are incompatible with long-term therapy (Zurlo J. et al 1990, Fertility and sterility 54: 64) Replacement therapy with C1 inhibitor has been tried for treatment in case of acute attacks. However, product isolated from plasma poses substantial risk of contamination. The plasma preparations of C1 inhibitor used at present are vapor-treated or pasteurized products. The heat treatment is a precaution to eliminate blood born infectious agents. Although taking the precautions for virus removal/inactivation there is still a risk for transmission of viruses such as HIV and hepatitis (De Filippi F. et al. 1998, Transfusion 38: 307). In addition to the safety problem the lack of availability of purified plasma C1 inhibitor as well as the high costs involved are disadvantages.

The production of functional C1 inhibitor in COS or CHO cells via recombinant DNA technology has been reported (see e.g. Eldering E. et al. 1988, J. Biol. Chem. 263: 11776). However, the reported yield in the µg/ml range is too low for therapeutic application. Expression of C1 inhibitor in microorganisms would not be expected to result in correct post-translational modification for functional inhibitor, and as far as we are aware, has not been attempted.

SUMMARY OF THE INVENTION

In one aspect, the invention provides transgenic nonhuman mammals expressing C1 inhibitor in their milk. Such mammals have a transgene comprising a recombinant DNA segment encoding a C1 inhibitor operably linked to at least one regulatory sequence effective to promote expression of the DNA segment in mammary gland cells of the transgenic nonhuman mammal and a segment encoding signal peptide functional in mammary secretory cells of the transgenic nonhuman mammal. The transgene, in an adult form of the nonhuman mammal or a female descendant of the nonhuman mammal, is capable of expressing the recombinant DNA segment in the mammary cells to produce a form of the C1 inhibitor that is secreted by the mammary secretory cells into milk of the nonhuman transgenic mammal. The C1 inhibitor is preferably human and preferably expressed in milk at a concentration of at least 1 mg/ml.

The invention is also directed to methods for providing C1 inhibitor. Such methods entail recovering milk from the adult form of the transgenic nonhuman mammal or its female descendant of claim 1 Optionally, the C1 inhibitor can be further purified from milk. In some methods, the C1 inhibitor is formulated with a pharmaceutical carrier as a pharmaceutical composition.

The invention further provides milk from a nonhuman animal comprising a human C1 inhibitor. The C1 inhibitor preferably has a concentration of at least 1 mg/ml and a functionality index of at least 0.9.

The invention further provides pharmaceutical compositions, comprising C1 inhibitor and a pharmaceutical carrier. The C1 inhibitor can be obtained from milk or other sources. In some such compositions, the human C1 inhibitor is free of other human proteins. In some composition, the human C1 inhibitor is at least 98% or 99% pure w/w.

The invention also provides methods of treating a patient suffering from or susceptible to C1 inhibitor deficiency using the above compositions.

In another aspect, the invention provides for the use of purified human C1 inhibitor in the manufacture of a medicament for treatment of a patient suffering from or susceptible to C1 inhibitor deficiency. In some uses, the human C1 inhibitor is free of other human proteins and in some methods, the human C1 inhibitor is at least 98% or 99% pure.

The invention further provides method of purifying human C1 inhibitor. Such method entail loading a sample comprising human C1 inhibitor onto a cationic exchange column under conditions in which the human C1 inhibitor binds to the column. Human C1 inhibitor is then eluted from the cationic exchange column. The eluate is loaded on an anionic exchange column under conditions in which the human C1 inhibitor binds to the column. The human C1 inhibitor is then eluted from the anionic exchange column. The eluate is loaded onto a metal ion exchange column under conditions in which residual contaminating proteins bind to the column. Eluate containing the human C1 inhibitor is then collected from the metal ion exchange column. The above method is particularly suitable for separating human C1 inhibitor from rabbit or other nonhuman C1 inhibitor.

DEFINITIONS

Figure 1A:
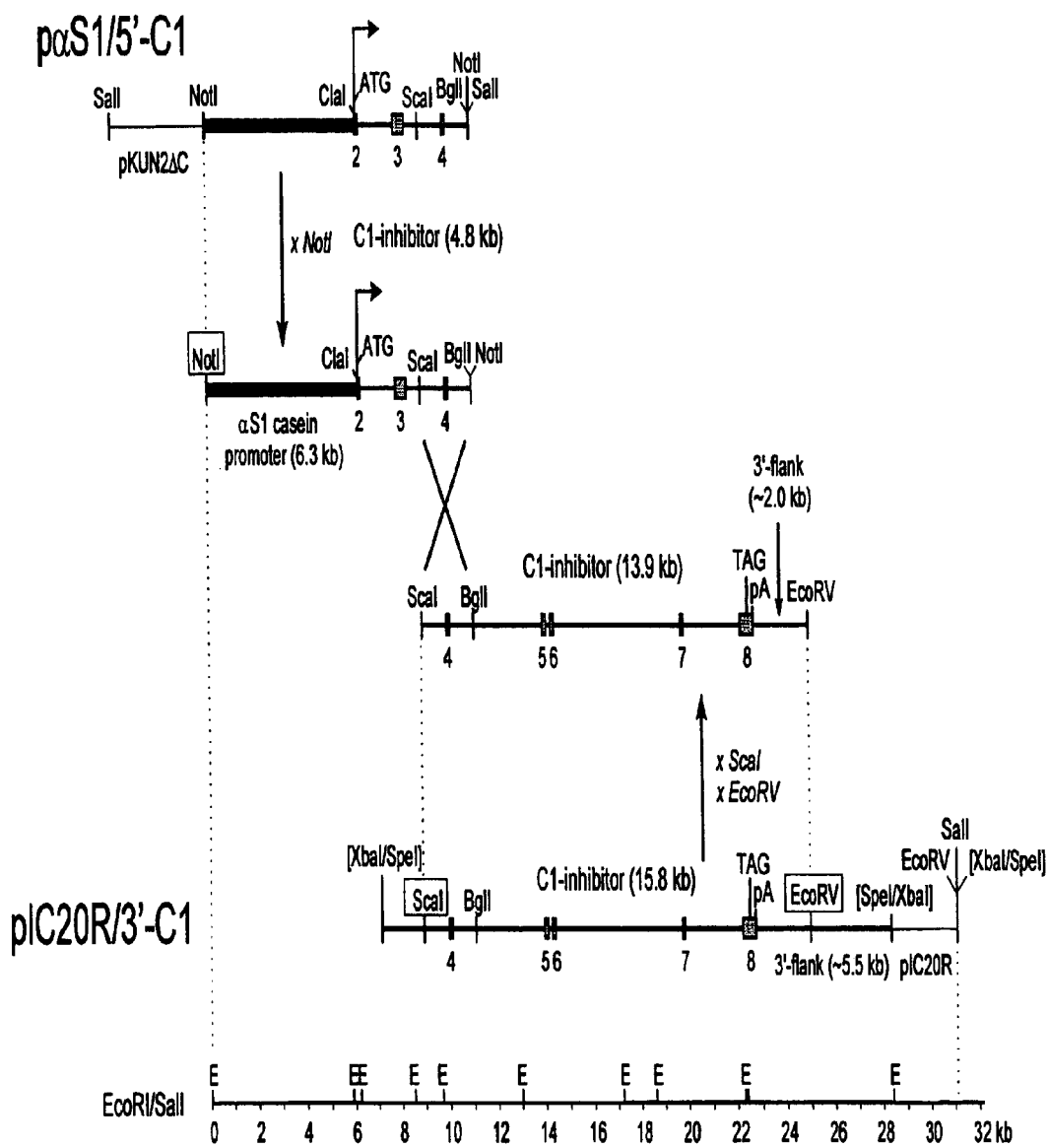
FIG. 1A. Schematic representation of the two overlapping fragments used for microinjection. The bovine αS1-casein promoter fragment is indicated by a black bar, the C1 inhibitor exons by grey bars, C1 inhibitor introns and flanking sequence by the thick black line. The site of recombination (overlap) is marked by the cross. It is not known whether there are EcoRI sites in the 3' flanking region.

The term "substantial identity" or "substantial homology" means that two peptide sequences, when optimally aligned, such as by the programs GAP or BESTFIT using default gap weights, share at least 65 percent sequence identity, preferably at least 80 or 90 percent sequence identity, more preferably at least 95 percent sequence identity or more (e.g., 99 percent sequence identity). Preferably, residue positions, which are not identical, differ by conservative amino acid substitutions.

The term "substantially pure" or "isolated" means an object species has been identified and separated and/or recovered from a component of its natural environment such as milk, nonhuman tissue culture cells or a natural source. For example, a substantially pure or isolated human C1 inhibitor produced by recombinant means in a non-human cells is free of other human proteins with which it existing in nature. Usually, the object species is the predominant species present (i.e., on a molar basis it is more abundant than any other individual species in the composition), and preferably a substantially purified fraction is a composition wherein the object species comprises at least about 50 percent (on a molar basis) of all macromolecular species present. Generally, a substantially pure composition will comprise more than about 80 to 90 percent by weight of all macromolecular species present in the composition and more preferably 90, 95, 99 or 99.9%. Most preferably, the object species is purified to essential homogeneity (contaminant species cannot be detected in the composition by conventional detection methods) wherein the composition consists essentially of derivatives of a single macromolecular species.

A DNA segment is operably linked when placed into a functional relationship with another DNA segment. For example, DNA for a signal sequence is operably linked to DNA encoding a polypeptide if it is expressed as a preprotein that participates in the secretion of the polypeptide; a promoter or enhancer is operably linked to a coding sequence if it stimulates the transcription of the sequence. Generally, DNA sequences that are operably linked are contiguous, and in the case of a signal sequence both contiguous and in reading phase. However, enhancers need not be contiguous with the coding sequences whose transcription they control. Linking is accomplished by ligation at convenient restriction sites or at adapters or linkers inserted in lieu thereof.

An exogenous DNA segment is one heterologous to the cell (e.g., from a different species than the cell), or homologous to a DNA segment of the cell but in an unnatural position in the host cell genome. Exogenous DNA segments are expressed to yield exogenous polypeptides.

In a transgenic mammal, all, or substantially all, of the germline and somatic cells contain a transgene introduced into the mammal or an ancestor of the mammal at an early embryonic stage.

The invention further provides a pharmaceutical composition comprising purified human C1 inhibitor. In some such compositions, the human C1 inhibitor is free of other human proteins. In some composition, the human C1 inhibitor is at least 98% or 99% pure w/w.

The invention also provides methods of treating a patient suffering from or susceptible to C1 inhibitor deficiency using the above compositions.

In another aspect, the invention provides for the use purified human C1 inhibitor in the manufacture of a medicament for treatment of a patient suffering from or susceptible to C1 inhibitor deficiency. In some uses, the human C1 inhibitor is free of other human proteins and in some methods, the human C1 inhibitor is at least 98% or 99% pure.

DETAILED DESCRIPTION

The present invention relates to efficient and safe production of C1 inhibitor in the milk of transgenic animals, purification of C1 inhibitor from milk or other sources, and therapeutic uses thereof. The results provided by the application show that C1 inhibitor can be produced in a very high concentration in the milk and in a form that is appropriately folded and posttranslationally modified to confer (enzyme) inhibitory activity. In contrast to plasma derived C1 inhibitor, C1 inhibitor produced via transgenic animals is free of risk for the transmission of blood-borne infectious agents. The animals used for the production of the transgenic product are a homogeneous population and can be controlled better than plasma donors thereby providing a much safer starting point for the isolation of C1 inhibitor. This makes the recombinant form of C1 inhibitor safer than the plasma product for clinical use.

The invention provides transgenic non-human mammals secreting C1 inhibitor into their milk. Secretion is achieved by incorporation of a transgene encoding a C1 inhibitor and at least one regulatory sequence capable of targeting expression of the gene to the mammary gland. The transgene is expressed, and, posttranslationally modified within the mammary gland, and then secreted in milk.

A. C1 Inhibitor Genes

The C1 inhibitor cDNA sequence was shown to encode a protein of 500 amino acids, including a 22 amino acid signal sequence (Bock et al. 1986, Biochem. 25: 4292–4301). The entire human genomic sequence of C1 inhibitor is known and shows that the gene comprises 7 introns (Carter P. et al. 1988, Eur. J. Biochem. 173: 163). Transgenic mammals expressing allelic, cognate and induced variants of any of the prototypical sequence described in this reference are included in the invention. Such variants usually show substantial sequence identity at the amino acid level with known C1 inhibitor genes. Such variants usually hybridize to a known gene under stringent conditions or cross-react with antibodies to a polypeptide encoded by one of the known genes. Other examples of genomic and cDNA sequences are available from GenBank. To the extent that additional cloned sequences of C1 inhibitor genes are required, they may be obtained from genomic or cDNA libraries (preferably human) using known C1 inhibitor sequences.

C. Transgene Design

Transgenes are designed to target expression of a recombinant C1 inhibitor to the mammary gland of a transgenic non-human mammal harboring the transgene. The basic approach entails operably linking an exogenous DNA segment encoding the protein with a signal sequence, and a regulatory sequence effective to promote expression of the exogenous DNA segment. Typically, the regulatory sequence includes a promoter and enhancer. The DNA segment can be genomic, minigene (genomic with one or more introns omitted), cDNA, a YAC fragment, a chimera of two different C1 inhibitor genes, or a hybrid of any of these. Inclusion of genomic sequences generally leads to higher levels of expression.

In genomic constructs, it is not necessary to retain all intronic sequences. For example, some intronic sequences can be removed to obtain a smaller transgene facilitating DNA manipulations and subsequent microinjection. See Archibald et al., WO 90/05188 (incorporated by reference in its entirety for all purposes). Removal of some introns is also useful in some instances to enhance expression levels. Removal of one or more introns to reduce expression levels to ensure that posttranslational modification is substantially complete may also be desirable. It is also possible to delete some or all of the non-coding exons. In some transgenes, selected nucleotides in C1 inhibitor encoding sequences are mutated to remove proteolytic cleavage sites.

Because the intended use of C1 inhibitors produced by transgenic mammals is usually administration to humans, the species from which the DNA segment encoding a C1 inhibitor sequence is obtained is preferably human. Analogously if the intended use were in veterinary therapy (e.g., on a horse, dog or cat), it is preferable that the DNA segment be from the same species.

Regulatory sequences such as a promoter and enhancer are from a gene that is exclusively or at least preferentially expressed in the mammary gland (i.e., a mammary-gland specific gene). Preferred genes as a source of promoter and enhancer include β-casein, κ-casein, αS1-casein, αS2-casein, β-lactoglobulin, whey acid protein, and α-lactalbumin. The promoter and enhancer are usually but not always obtained from the same mammary-gland specific gene. Preferably this gene is from the same species of mammal as the mammal into which the transgene is to be expressed. Expression regulation sequences from other species such as those from human genes can also be used. The signal sequence must be capable of directing the secretion of the C1 inhibitor from the mammary gland. Suitable signal sequences can be derived from mammalian genes encoding a secreted protein. The natural signal sequences of C1 inhibitors are suitable. In addition to such signal sequences, preferred sources of signal sequences are the signal sequence from the same gene as the promoter and enhancer are obtained. Optionally, additional regulatory sequences are included in the transgene to optimize expression levels. Such sequences include 5' flanking regions, 5' transcribed but untranslated regions, intronic sequences, 3' transcribed but untranslated regions, polyadenylation sites, and 3' flanking regions. Such sequences are usually obtained either from the mammary-gland specific gene from which the promoter and enhancer are obtained or from the C1 inhibitor gene being expressed. Inclusion of such sequences produces a genetic milieu simulating that of an authentic mammary gland specific gene and/or that of an authentic C1 inhibitor gene. This genetic milieu results in some cases (e.g., bovine αS1-casein) in higher expression of the transcribed gene. Alternatively, 3' flanking regions and untranslated regions are obtained from other heterologous genes such as the β-globin gene or viral genes. The inclusion of 3' and 5' untranslated regions from a C1 inhibitor gene, or other heterologous gene can also increase the stability of the transcript.

In some embodiments, about 0.5, 1, 5, 10, 15, 20 or 30 kb of 5' flanking sequence is included from a mammary specific gene in combination with about 1, 5, 10, 15, 20 or 30 kb or 3' flanking sequence from the C1 inhibitor gene being expressed. If the protein is expressed from a cDNA sequence, it is advantageous to include an intronic sequence between the promoter and the coding sequence. The intronic sequence is preferably a hybrid sequence formed from a 5' portion from an intervening sequence from the first intron of the mammary gland specific region from which the promoter is obtained and a 3' portion from an intervening sequence of an IgG intervening sequence or C1 inhibitor gene. See DeBoer et al., WO 91/08216 (incorporated by reference in its entirety for all purposes). Another preferred transgene for expressing a C1 inhibitor cDNA is based on the pBC1 expression vector kit, which is commercially available from Invitrogen (Carlsbad, Calif.). The pBC1 vector comprises the goat β-casein promoter as well as parts of the goat β-casein gene, which include several exons and introns, as well as 3' untranslated sequences. Insertion of the C1 inhibitor cDNA into the unique XhoI insertion site of pBC1 will produce a chimeric RNA comprising the C1 inhibitor cDNA sequences flanked by the goat β-casein exon and intron sequences. However, upon proper splicing of this chimeric RNA molecule, only the C1 inhibitor cDNA sequences is translated.

A preferred transgene for expressing a C1 inhibitor protein from genomic sequences comprises a genomic C1 inhibitor sequence encoding the entire coding sequence and a signal peptide, a 3' UTR and a 3' flanking sequence, operably linked to a 5' alpha S1 casein fragment containing regulatory sequence(s) sufficient to direct expression of the C1 inhibitor protein.

DNA sequence information is available for all of the mammary gland specific genes listed above, in at least one, and often several organisms. See, e.g., Richards et al., J. Biol. Chem. 256, 526–532 (1981) (α-lactalbumin rat); Campbell et al., Nucleic Acids Res. 12, 8685–8697 (1984) (rat WAP); Jones et al., J. Biol. Chem. 260, 7042–7050 (1985)) (rat β-casein); Yu-Lee & Rosen, J. Biol. Chem. 258,10794–10804 (1983) (rat γ-casein)); Hall, Biochem. J. 242, 735–742 (1987) (α-lactalbumin human); Stewart, Nucleic Acids Res. 12, 389 (1984) (bovine αs1 and κ casein cDNAs); Gorodetsky et al., Gene 66, 87–96 (1988) (bovine β casein); Alexander et al., Eur. J. Biochem. 178, 395–401 (1988) (bovine κ casein); Brignon et al., FEBS Lett. 188, 48–55 (1977) (bovine αS2 casein); Jamieson et al., Gene 61, 85–90 (1987), Ivanov et al., Biol. Chem. Hoppe-Seyler 369, 425–429 (1988), Alexander et al., Nucleic Acids Res. 17, 6739 (1989) (bovine β lactoglobulin); Vilotte et al., Biochimie 69, 609–620 (1987) (bovine α-lactalbumin) (incorporated by reference in their entirety for all purposes). The structure and function of the various milk protein genes are reviewed by Mercier & Vilotte, J. Dairy Sci. 76, 3079–3098 (1993) (incorporated by reference in its entirety for all purposes). To the extent that additional sequence data might be required, sequences flanking the regions already obtained could be readily cloned using the existing sequences as probes. Mammary-gland specific regulatory sequences from different organisms are likewise obtained by screening libraries from such organisms using known cognate nucleotide sequences, or antibodies to cognate proteins as probes.

General strategies and exemplary transgenes employing αS1-casein regulatory sequences for targeting the expression of a recombinant protein to the mammary gland are described in more detail in DeBoer et al., WO 91/08216 and WO 93/25567 (incorporated by reference in their entirety for all purposes). Examples of transgenes employing regulatory sequences from other mammary gland specific genes have also been described. See, e.g., Simon et al., Bio/Technology 6, 179–183 (1988) and WO 88/00239 (1988) (β-lactoglobulin regulatory sequence for expression in sheep); Rosen, EP 279,582 and Lee et al., Nucleic Acids Res. 16, 1027–1041 (1988) (β-casein regulatory sequence for expression in mice); Gordon, Biotechnology 5, 1183 (1987) (WAP regulatory sequence for expression in mice); WO 88/01648 (1988) and Eur. J. Biochem. 186, 43–48 (1989) (α-lactalbumin regulatory sequence for expression in mice) (incorporated by reference in their entirety for all purposes).

D. Transgenesis

The transgenes described above are introduced into non-human mammals. Most non-human mammals, including rodents such as mice and rats, rabbits, ovines such as sheep, caprines such as goats, porcines such as pigs, and bovines such as cattle and buffalo, are suitable. Bovines offer an advantage of large yields of milk, whereas mice offer advantages of ease of transgenesis and breeding. Rabbits offer a compromise of these advantages. A rabbit can yield 100 ml milk per day with a protein content of about 14% (see Buhler et al., Bio/Technology 8, 140 (1990)) (incorporated by reference in its entirety for all purposes), and yet can be manipulated and bred using the same principles and with similar facility as mice. Nonviviparous mammals such as a spiny anteater or duckbill platypus are typically not employed.

In some methods of transgenesis, transgenes are introduced into the pronuclei of fertilized oocytes. For some animals, such as mice and rabbits, fertilization is performed in vivo and fertilized ova are surgically removed. In other animals, particularly bovines, it is preferable to remove ova from live or slaughterhouse animals and fertilize the ova in vitro. See DeBoer et al., WO 91/08216. In vitro fertilization permits a transgene to be introduced into substantially synchronous cells at an optimal phase of the cell cycle for integration (not later than S-phase). Transgenes are usually introduced by microinjection. See U.S. Pat. No. 4,873,292. Fertilized oocytes are then cultured in vitro until a pre-implantation embryo is obtained containing about 16–150 cells. The 16–32 cell stage of an embryo is described as a morula. Pre-implantation embryos containing more than 32 cells are termed blastocysts. These embryos show the development of a blastocoele cavity, typically at the 64-cell stage. Methods for culturing fertilized oocytes to the pre-implantation stage are described by Gordon et al., Methods Enzymol. 101, 414 (1984); Hogan et al., Manipulation of the Mouse Embryo: A Laboratory Manual, C.S.H.L. N.Y. (1986) (mouse embryo); Hammer et al., Nature 315, 680 (1985) (rabbit and porcine embryos); Gandolfi et al. J. Reprod. Fert. 81, 23–28 (1987); Rexroad et al., J. Anim. Sci. 66, 947–953 (1988) (ovine embryos) and Eyestone et al. J. Reprod. Fert. 85, 715–720 (1989); Camous et al., J. Reprod. Fert. 72, 779–785 (1984); and Heyman et al. Theriogenology 27, 5968 (1987) (bovine embryos) (incorporated by reference in their entirety for all purposes). Sometimes pre-implantation embryos are stored frozen for a period pending implantation. Pre-implantation embryos are transferred to the oviduct of a pseudopregnant female resulting in the birth of a transgenic or chimeric animal depending upon the stage of development when the transgene is integrated. Chimeric mammals can be bred to form true germline transgenic animals.

Alternatively, transgenes can be introduced into embryonic stem cells (ES). These cells are obtained from preimplantation embryos cultured in vitro. Bradley et al., Nature 309, 255–258 (1984) (incorporated by reference in its entirety for all purposes). Transgenes can be introduced into such cells by electroporation or microinjection. ES cells are suitable for introducing transgenes at specific chromosomal locations via homologous recombination. For example, a transgene encoding C1 inhibitor can be introduced at a genomic location at which it becomes operably linked to an endogenous regulatory sequence that can directed expression of the coding sequence in the mammary gland. Transformed ES cells are combined with blastocysts from a non-human animal. The ES cells colonize the embryo and in some embryos form or contribute to the germline of the resulting chimeric animal. See Jaenisch, Science, 240, 1468–1474 (1988) (incorporated by reference in its entirety for all purposes). Alternatively, ES cells can be used as a source of nuclei for transplantation into an enucleated fertilized oocyte, giving rise to a transgenic mammal.

In a further embodiment, transgenic animals, preferably non-human mammals, containing a transgenes capable of expressing C1 inhibitor are produced by methods involving nuclear transfer. Various types of cells can be employed as donors for nuclei to be transferred into oocytes. Donor cells can be obtained from all tissues of transgenic animals containing a C1 inhibitor transgenes, such as adult, fetal or embryonic cells, at various stages of differentiation, ranging from undifferentiated to fully differentiated, in various cell cycle stages, e.g. both quiescent and proliferating cells, and obtained form either somatic or germline tissues (see WO 97/07669, WO 98/30683 and WO 98/39416, each incorporated by reference in their entirety for all purposes). Alternatively, donor nuclei are obtained from cells cultured in vitro into which a C1 inhibitor transgene is introduced using conventional methods such as Ca-phosphate transfection, microinjection or lipofection and which have subsequently been selected or screened for the presence of a transgene or a specific integration of a transgene (see WO 98/37183 and WO 98/39416, each incorporated by reference in their entirety for all purposes). Donor nuclei are introduced into oocytes by means of fusion, induced electrically or chemically (see any one of WO 97/07669, WO 98/30683 and WO 98/39416), or by microinjection (see WO 99/37143, incorporated by reference in its entirety for all purposes). Transplanted oocytes are subsequently cultured to develop into embryos which are subsequently implanted in the oviducts of pseudopregnant female animals, resulting in birth of transgenic offspring (see any one of WO 97/07669, WO 98/30683 and WO 98/39416).

Another method of transgenesis uses (retro)virus-based vectors to introduce the desired transgenes. Examples of such vectors include the vesicular stomatitis virus G glycoprotein (VSG-G) MoMLV derived retroviral vector (VSV-G pseudotype) as described by Yee et al. (1994, Meth. Cell. Biol. 43: 99–112, incorporated by reference in its entirety for all purposes). Non-human mammalian, preferably bovine, oocytes arrested in metaphase II of the second meiotic division before fertilization are infected with such a VSV-G pseudotype vector as described by Chan et al (1998, Proc. Natl. Acad. Sci. USA 95: 14028–14033, incorporated by reference in its entirety for all purposes) to produce transgenic offspring. Alternatively, instead of producing a genetically modified animal, a restricted organ, preferably a mammary gland is transformed by retroviral infection for the purpose of making pharmaceutical proteins. Infusion retroviral vectors, carrying sequences encoding C1 inhibitor, into non-human mammary glands to infect the mammary epithelial cells allow the production of the C1 inhibitor protein in the milk of these animals (Archer et al., 1994, Proc. Natl. Acad. Sci. USA 91: 6840–6844, incorporated by reference in its entirety for all purposes).

For production of transgenic animals containing two or more transgenes, the transgenes can be introduced simultaneously using the same procedure as for a single transgene. Alternatively, the transgenes can be initially introduced into separate animals and then combined into the same genome by breeding the animals. Alternatively, a first transgenic animal is produced containing one of the transgenes. A second transgene is then introduced into fertilized ova or embryonic stem cells from that animal. In some embodiments, transgenes whose length would otherwise exceed about 50 kb, are constructed as overlapping fragments. Such overlapping fragments are introduced into a fertilized oocyte or embryonic stem cell simultaneously and undergo homologous recombination in vivo. See Kay et al., WO 92/03917 (incorporated by reference in its entirety for all purposes).

E. Characteristics of Transgenic Mammals

Transgenic mammals of the invention incorporate at least one transgene in their genome as described above. Introduction of a transgene at the one cell stage usually results in transgenic animals and their progeny substantially all of whose germline and somatic cells (with the possible exception of a few cells that have undergone somatic mutations) contain the transgene in their genomes. Introduction of a transgene at a later stage leads to mosaic or chimeric animals. However, some such animals that have incorporated a transgene into their germline can be bred to produce transgenics substantially all of whose somatic and germline cells contain a transgene. Viral transgenesis of mammary gland cells usually results in a transgenic mammal in which the transgene is present only in mammary gland cells. Such a mammal does not transmit its germline to future generations. The transgene targets expression of a DNA segment encoding a C1 inhibitor protein at least predominantly to the mammary gland. C1 inhibitor can be secreted at high levels of at least 100, 500, 1000, 2000, 5000 or 10,000, 20,000 or 50,000 µg/ml. Surprisingly, the transgenic mammals of the invention exhibit substantially normal health. Secondary expression of C1 inhibitor proteins in tissues other than the mammary gland does not occur to an extent sufficient to cause deleterious effects. Moreover, exogenous C1 inhibitor protein is secreted from the mammary gland with sufficient efficiency that no problem is presented by deposits clogging the secretory apparatus.

The age at which transgenic mammals can begin producing milk, of course, varies with the nature of the animal. For transgenic bovines, the age is about two-and-a-half years naturally or six months with hormonal stimulation, whereas for transgenic mice the age is about 9–11 weeks. Of course, only the female members of a species are useful for producing milk. However, transgenic males are also of value for breeding female descendants. The sperm from transgenic males can be stored frozen for subsequent in vitro fertilization and generation of female offspring.

F. Recovery of Proteins from Milk or Other Sources

Transgenic adult female mammals produce milk containing high concentrations of exogenous C1 inhibitor protein. Purification of C1 inhibitor from milk can be carried out by defatting of the transgenic milk by centrifugation and removal of the fat, followed by removal of casein's by high speed centrifugation followed by dead-end filtration (i.e., dead-end filtration by using successively declining filter sizes) or cross-flow filtration, or; removal of casinos directly by cross filtration. The protein can be purified from milk, if desired, by virtue of its distinguishing physical and chemical properties (see generally Scopes, Protein Purification (Springer-Verlag, N.Y., 1982)) Prograis et al., (1985) J. Medicine 16 (1–3): 303–350; Pilatte et al., (1989) J. Immunol. Methods 120: 37–43, Reboul et al.,. (1977) Febs Lett. 79: 45–50, Alsenz et al., (1987) J. Immunol. Methods 96: 107–114, Ishizaki et al., (1977) J. Biochem. 82: 1155–1160. The conditions of purification should preferably separate human C1 inhibitor from endogenous C1 inhibitor of the nonhuman transgenic mammal.

Cationic, anionic and metal-affinity chromatography can all be used for purification of human C1 inhibitor protein, from milk or other sources, such as recombinant cell cultures or natural sources. Some methods use more than one of these steps, and some methods use all three steps. Although the steps can be performed in any order, a preferred order is to perform cationic chromatography, followed by anionic chromatography, followed by metal ion affinity chromatography.

Cationic chromatography can be performed, for example, using Sepharose(™)big beads or carboxymethyl-cellulose. A low salt loading buffer (e.g., 20 mM sodium citrate, 0.02 M sodium chloride) is used. Human C1 inhibitor can be eluted at higher salt concentration (e.g., 20 mM sodium citrate, 0.2 M sodium chloride). Eluate containing human C1 inhibitor is then subject to anionic chromatography.

The matrix of an anionic column can be a material such as cellulose, dextrans, agarose or polystyrene. The ligand can be eithylaminoethyl (DEAE), polyethyleneimine (PEI) or a quaternary ammonium functional group example. The strength of an anion exchange column refers to the state of ionization of the ligand. Strong ionic exchange columns, such as those having a quaternary ammonium ligand, bear a permanent positive charge. In weak anion exchange columns, such as DEAE and PEI, the existence of the positive charge depends on the pH of the column. Anion exchange columns are generally loaded with a low-salt buffer at a pH above the pI of human C1 inhibitor ( ). The columns are washed several times in the low-salt buffer to elute proteins that do not bind. Proteins that have bound are then eluted using a buffer of increased salt concentration. Q Sepharose FF is a preferred anion exchange column because this material is relatively inexpensive compared with other anion-exchange columns and has a relatively large bead size suitable for large scale purification. Under specified conditions, human C1 inhibitor can be eluted from Q Sepharose FF without eluting rabbit C1 inhibitor or other proteins found in rabbit milk. To obtain good binding of human acid α-glucosidase to the Q Sepharose FF, the column is pre-equilibrated in low salt (i.e., less than 50 mM, such as sodium phosphate buffer. The pH of the buffer should be about 7.0+/−1.0 to obtain a good binding of human C1 inhibitor to the column. Human C1 inhibitor is then eluted by step-wise or gradient elution at increased salt concentration. Step-wise elution is more amenable to large-scale purification. Most loaded human C1 inhibitor can be eluted from a Q FF column in one step (at about 0.25 M salt) with relatively high purity.

Metal affinity chromatography is conducted using a matrix, such as Sepharose(™), and a bound metal ion, such as copper, zinc, nichol, cobalt or calcium. Organic chelating groups such as iminodiacetic acid can also be used. The column is equilibrated at a pH of about 6–8 with a nonchelating salt (e.g., sodium chloride) present at a relatively high concentration e.g., greater than 0.2 M. Under these conditions, residual contaminating proteins bind to the column, whereas human C1 inhibitor does not, and can be readily eluted.

An exemplary purification procedure is described in the Examples section. This procedure provides a C1 inhibitor preparation, which is at least 98% or 99% pure (w/w) with respect to all contaminants and contains less than 0.5%, 0.1% or 0.05% rabbit C1 inhibitor (w/w). Additional purification are preferably used to obtain C1 inhibitor preparations with a purity of at least 99%, preferably at least 99.5%, more preferably 99.8% and most preferably 99.9%.

G. Uses of Recombinant C1 Inhibitor

C1 inhibitor purified from milk or other sources finds use in replacing or supplementing endogenous C1 inhibitor in patients suffering from hereditary angioedema, a disease characterized by absence or deficiency in endogenous functional C1 inhibitor. A patient having a genetic or other deficiency resulting in an insufficiency of functional C1 inhibitor can be treated by administering exogenous C1 inhibitor to the patient. Patients in need of such treatment can be identified from non-pitting subepithelial edema resulting from a local increase in vasopermeability (Cicardi M. et al 1998, Immunobiol. 199: 366). The three sites primarily involved are: subcutaneous tissue (extremities, face, genitals, buttocks), abdominal organs and the upper airway (larynx). Swelling of the mucosa of the abdominal can be very painful and laryngeal edema is a life-threatening situation.

Alternatively, or additionally, patients can be diagnosed from biochemical analysis. Diagnostic assays are often performed on blood plasma and comprise C1 inhibitor functional and antigenic assays, and determination of complement components C4 and C2 levels. Complement components C4 and C2 levels are generally strongly reduced during attacks of angioedema, and sometimes also between attacks, although to a lesser extent. Complement components C4 and C2 levels are reduced due to ongoing activation and consumption of the C4 and C2 components by C1 esterase. In patients with acquired angioedema, complement component C1 or subcomponent C1q are generally reduced next to component C4 and C2 levels. Hereditary angioedema patients can be classified type I or type II patients. The more common type I deficiency is characterized by low levels of circulating C1 inhibitor, resulting from genetic lesions that abolish expression of the affected allele (see Tosi, M., 1998, Immunobiol. 199: 358–365). Type II deficiency, with normal levels of C1 inhibitor antigen, is predominantly caused by point mutations resulting in the expression of a dysfunctional protein (Tosi, M., 1992, "Molecular genetics of C1 inhibitor and hereditary angioedema" In: Complement in health and disease. 2nd ed., Whaley, Loos and Weiler, eds.). Patients can also be diagnosed by detecting homozygous or heterozygous mutations in the C1 inhibitor gene. Diagnosis is preferably made by detecting C1 inhibitor deficiency or by DNA analysis before occurrence of symptoms. In offspring from families known to have members suffering from hereditary angioedema, it is sometimes advisable to commence prophylactic treatment even before a definitive diagnosis can be made.

Pharmaceutical Compositions

In some methods, C1 inhibitor purified from milk or other source is administered in purified form together with a pharmaceutical carrier as a pharmaceutical composition. The preferred form depends on the intended mode of administration and therapeutic application. The pharmaceutical carrier can be any compatible, nontoxic substance suitable to deliver the polypeptides to the patient. Sterile water, alcohol, fats, waxes, and inert solids may be used as the carrier. Pharmaceutically acceptable adjuvants, buffering agents, dispersing agents, and the like, may also be incorporated into the pharmaceutical compositions.

The concentration of the inhibitor in the pharmaceutical composition can vary widely, i.e., from less than about 0.1% by weight, usually being at least about 1% by weight to as much as 20% by weight or more.

For oral administration, the active ingredient can be administered in solid dosage forms, such as capsules, tablets, and powders, or in liquid dosage forms, such as elixirs, syrups, and suspensions. Active component(s) can be encapsulated in gelatin capsules together with inactive ingredients and powdered carriers, such as glucose, lactose, sucrose, mannitol, starch, cellulose or cellulose derivatives, magnesium stearate, stearic acid, sodium saccharin, talcum, magnesium carbonate and the like. Examples of additional inactive ingredients that may be added to provide desirable color, taste, stability, buffering capacity, dispersion or other known desirable features are red iron oxide, silica gel, sodium lauryl sulfate, titanium dioxide, edible white ink and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric-coated for selective disintegration in the gastrointestinal tract. Liquid dosage forms for oral administration can contain coloring and flavoring to increase patient acceptance.

C1 inhibitor is preferably administered parentally. C1 inhibitor preparations for parental administration must be sterile. Sterilization is readily accomplished by filtration through sterile filtration membranes, prior to or following lyophilization and reconstitution. The parental route for C1 inhibitor administration is in accord with known methods, e.g. injection or infusion by intravenous, intraperitoneal, intracerebral, intramuscular, intraocular, intraarterial or intralesional routes. C1 inhibitor is administered continuously by infusion or by bolus injection. A typical composition for intravenous infusion could be made up to contain 100 to 500 ml of sterile 0.9% NaCl or 5% glucose optionally supplemented with a 20% albumin solution and 100 to 500 mg of the C1 inhibitor. A typical pharmaceutical composition for intramuscular injection would be made up to contain, for example, 1–10 ml of sterile buffered water and 1 to 100 mg of the C1 inhibitor of the present invention. Methods for preparing parenterally administrable compositions are well known in the art and described in more detail in various sources, including, for example, Remington's Pharmaceutical Science (15th ed., Mack Publishing, Easton, Pa., 1980) (incorporated by reference in its entirety for all purposes).

Therapeutic Methods

The present invention provides effective methods of treating C1 inhibitor deficiency using exogenous C1 inhibitor. C1 inhibitor can also be used to treat other diseases in which classical pathway complement activity (activated C1 component) and/or contact system (factor XIIa, kallikrein, factor XIa) activity contributes to undesired immune or inflammatory responses. Such diseases include myocardial infarction (WO 95/06479); acquired systemic inflammatory responses among which severe sepsis, septic shock, ARDS (Adult Respiratory Distress Syndrome), multiple organ failure and preeclampsia (WO 92/22320: Genentech Inc); capillary leakage syndrome and circulatory failure in cases of severe burns, polytraumata, operations with extracorporeal circulation (EP 0586909), therapeutic cytokine (e.g. IL2) infusion, acute graft versus host disease after allogeneic (or autologic) bone marrow transplantation. Other indications may be disorders in which excess classical route complement and/or contact activation, and/or C1 inhibitor consumption or (relative) functional C1 inhibitor deficiency has been implicated in the pathophysiology, such as meningitis, rheumatoid arthritis, hyper acute graft rejection after allo- and xeno-transplantation and pancreatitis.

The pharmaceutical compositions of the present invention are usually administered intravenously. Intradermal, intramuscular or oral administration is also possible in some circumstances. The compositions can be administered for prophylactic treatment of individuals suffering from, or at risk of, a disease in an amount sufficient to prevent, delay or reduce the severity of subsequent disease. For therapeutic applications, the pharmaceutical compositions are administered to a patient suffering from established disease in an amount sufficient to reduce the severity of symptoms and/or prevent or arrest further development of symptoms. An amount adequate to accomplish this is defined as a "therapeutically-" or "prophylactically-effective dose." Such effective dosages will depend on the severity of the condition and on the general state of the patient's health. One effective dosage is that necessary to achieve a plasma concentration of at least about 50 µg functional C1 inhibitor per ml plasma, preferably at least about 100 µg functional C1 inhibitor per ml plasma, more preferably at least about 200 µg functional C1 inhibitor per ml plasma, and most preferably at least about 250 µg functional C1 inhibitor per ml plasma. Typically these plasma concentrations of functional C1 inhibitor are maintained for at least 1 hour, preferably at least 4 hours, more preferably at least 12 hours, and most preferably at least 24 hours.

In the present methods, C1 inhibitor is usually administered at a dosage of about 10 mg/kg patient body weight or more per week to a patient. Often dosages are greater than 10 mg/kg per week. Dosage regimes can range from 10 mg/kg per week to at least 1000 mg/kg per week. Typically dosage regimes are 10 mg/kg per week, 20 mg/kg per week, 30 mg/kg per week, 40 mg/kg week, 60 mg/kg week, 80 mg/kg per week and 120 mg/kg per week. In preferred regimes 10 mg/kg, 20 mg/kg or 40 mg/kg is administered once, twice or three times weekly. Treatment is typically continued for at least 4 weeks, sometimes 24 weeks, and sometimes for the life of the patient. Treatment is preferably administered by intravenous route. Optionally, levels of C1 inhibitor are monitored following treatment (e.g., in the plasma) and a further dosage is administered when detected levels fall substantially below e.g., less than 40%, less than 30%, or less than 20% of values in normal persons. Alternatively, in some conditions it may be desirable to achieve higher than normal levels, e.g. 150% of normal levels, 200% of normal levels or even 300% of normal levels.

Other Uses

C1 inhibitor produced in the milk of transgenic animals has a number of other uses. For example, C1 inhibitor can be used as a control reagent in kits for in vitro diagnosis of endogenous C1 inhibitor activity. Alternatively, C1 inhibitor may be immobilized on extracorporal devices to selectively remove anti-C1 inhibitor antibodies from patients.

EXAMPLES

Example 1

Construction of Transgenes a. Overlapping Genomic Constructs (CINHI1)

A set of two expression vectors containing overlapping parts of the genomic sequence of the human C1 inhibitor gene was constructed. Together these plasmids contain the bovine αS1-casein promoter and the complete human C1 inhibitor genomic sequence. All C1 inhibitor fragments used were derived from P1 clone DMDC-HFF#1-1112-69, obtained from Genome Systems Inc. (8620 Pennell Drive, St. Louis, Mo. 63114), which was isolated from a P1 human genomic library by PCR with two C1 inhibitor specific primers (Appendix 1A).

Plasmid pαS1/5'C1, which includes 6.3 kb of bovine αS1-casein regulatory sequences fused to the 5'-part of the C1 inhibitor gene, was constructed as follows. First, pKUN1 [Konings, 1986 Gene 46,269–76] was digested with EcoRI and SalI and ligated to linker 1 (Appendix 1B), followed by removal of the ClaI site by filling in with Klenow and ligating. From the resulting plasmid pKUN2ΔC, pKUN2ΔCNBS was made by ligating linker 2 (Appendix 1C) into the NotI and SalI sites. Linker 2 provided a ClaI site, 19 bp of αS1-casein exon 1 (with the first C mutated to a T to prevent methylation of the ClaI site), the 6 bp normally flanking the C1 inhibitor ATG translation start site, and a SfiI site compatible with the BglI site in the C1 inhibitor gene that overlaps the ATG. Then linker 3 (Appendix 1D) was ligated into the SfiI and MluI sites of pKUN2ΔCNBS, resulting in plasmid pKUN2ΔCEV. Linker 3 introduced a second SfiI site compatible to the next BglI site in the C1 inhibitor gene, situated 4.8 kb downstream of the ATG, and a NotI site. Subsequently, the 4.8 kb BglI fragment was cloned from the P1 clone (supra) into the dephosphorylated SfiI sites of plasmid pKUN2ΔCEV, resulting in pK-BglI-C1This construct lacks exon 1 and the first 16 bp from exon 2, which together form most of the C1 inhibitor 5' UTR (untranslated region) but still contains the ATG translational start codon, which is located in exon 2. From this plasmid, the 4.85 kb ClaI-SalI fragment was cloned into plasmid p(−8 kb,CS) (Patent application WO 93/25567), resulting in plasmid pαS1/5'-C1. This links the C1 inhibitor fragment to the 6.2 kb NotI-ClaI bovine αS1-casein promoter fragment which includes the first 20 bp from αS1-casein exon 1 (EMBL database, accession number X59856; [Koczan, 1991, Nucleic Acids Res. 19, 5591–5596]), directly flanked by the ClaI site used in the cloning step.

The second vector, pIC20R/3'-C1 was made by digestion of the P1 clone (supra) with SpeI, followed by ligation of the 20 kb SpeI fragment containing exons 4–8 plus approximately 5.5 kb of 3' flanking DNA, into the dephosphorylated XbaI site of pIC20R [Marsh, 1984 Gene 32, 481–485]. The overlap between pαS1/5'-C1 and pIC20R/3'-C1 was 2.0 kb.

b. Single Genomic Construct (CINH2).

A single construct containing the complete human C1 inhibitor gene fused to the bovine αS1-casein promoter was also made. First, plasmid pK-BglI-C1 inhibitor (supra) was digested with SpeI and SalI and ligated to linker 4 (Appendix 1E), yielding plasmid pK-BgSpL-C1. Then, the 20 kb SpeI fragment from the P 1 clone (supra) was cloned into pK-BgSpL-C1 digested with SpeI and dephosphorylated. From the resulting vector, named pCBSpeIC1, a 22 kb ClaI-SalI fragment containing the entire C1 inhibitor coding region plus 5.5 kb of 3'-flanking DNA, was ligated into p(−8 kb,CS) (supra) digested with ClaI and SalI. The final construct was named p6,2C1-INH2.

Example 2

Transgenesis

A. Overlapping Constructs (CINH1) in Mice.

Transgenic mice were produced by pronuclear injection of fertilized oocytes, essentially as described by Hogan et al., 1986, "Manipulating the Mouse Embryo", Cold Spring Harbour Press NY. pαS1-5'C1 (see FIG. 1A) was digested with NotI, yielding an 11.3 kb fragment which was isolated by gelpurification and electroelution. Similarly, a 15.8 kb ScaI-EcoRV fragment from pIC20R/3'-C1, extending from intron 3 to 2 kb beyond the last exon, was prepared. Both fragments were combined (at a concentration of 3 ng/μl) and injected into the pronucleus of fertilized mouse oocytes, which were implanted in the uterus of pseudopregnant mouse foster mothers. The offspring was analyzed for the insertion of the human C1 inhibitor genomic gene construct by Southern blotting of DNA isolated from clipped tails. Whether correct homologous recombination between the overlapping fragments had occurred, was checked on Southern blots and by PCR. 33 transgenic mice were obtained, 31 of which contained correctly recombined transgenes. 17 of these 31 mice were selected for further breeding using FISH analysis to exclude animals with multiple integration sites and/or a high level of mosaicism.

Figure 1B:
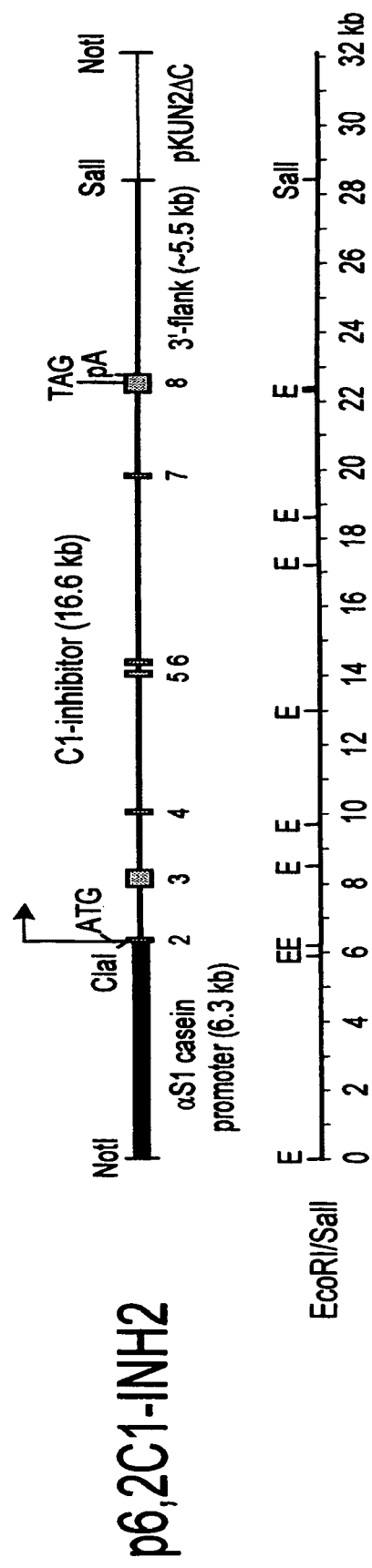
FIG. 1B. Schematic representation of the single genomic fragment used for microinjection.

B. Single Genomic Construct (CINH2) in Mice.

p6,2C1-INH2 was digested with NotI and SalI, yielding a 28.2 kb fragment (FIG. 1B). A solution of this fragment at a concentration of 3 ng/μl was used for microinjection into mouse oocytes, as described above. 30 transgenic mice were obtained, 12 of which were selected for further breeding by FISH analysis.

C. Single Genomic Construct (CINH2) in Rabbits.

Transgenic rabbits were generated according to the following protocol. Each female donor animal (New Zealand White) was treated subcutaneously for 3 days with porcine FSH (Sigma). On the first and second day, 0.5 U was injected at approx. 8 am and 6 pm. On the third day, 0.5 U were injected at approx. 8 am and at 11 pm. On the fourth day, the females were mated (to New Zealand White sires) at 2 pm. Directly following the mating the females were injected intramuscularly with 150 U Pregnil (human; Organon). On the fifth day the donor animals were sacrificed at 9 am by an intravenous injection of T61 (Hoechst Roussel Vet) and the embryos collected by flushing. By using the relatively long delay between mating and the sacrifice of the animals, there was no need for treating the embryos with hyaluronidase nor for microdissection to remove surrounding cells which were spontaneously released. Embryos were maintained in RD medium (1:1 (v/v) mixture of RPMI-1640 and Dulbecco's Modified Eagle's Medium (high glucose modification) supplemented with 100 U penicillin-G/ml, 100 mg streptomycin sulfate/ml and 15 mg Fraction V BSA/ml; Carney E. W. and Foote R. H. (1991) J. Reprod. Fert. 91:113–123) at 39° C. Microinjections (2–3 picoliter per oocyte) were carried out immediately and the embryos were reimplanted in both oviducts (10–15 embryos on each side) of recipient females. The recipient females were prepared by subcutaneous injection of 15 U horse Folligon (Intervet) on day 2. On the fourth day, the recipient females received an intramuscular injection with 0.33 ml Receptal (0.0014 mg buserelini, Hoechst Roussel Vet.).

Initially, a few rabbits were generated using the overlapping constructs. PCR analysis showed that not only the correctly recombined transgene was present but also non-recombined, ligated 5' and 3' fragments. In such a configuration, exon 4 is duplicated. Rearranged copies of the transgene are undesirable, as they may give rise to aberrant transcripts and, hence, to deviant protein molecules. Therefore, it was decided to only use the single genomic construct for the generation of transgenic rabbits for commercial C1 inhibitor production.

p6,2C1-INH2 was digested with NotI and SalI, yielding a 28.2 kb fragment (FIG. 1B). A solution of this fragment at a concentration of 3 ng/μl was used for microinjection into fertilized rabbit oocytes. Ten transgenic rabbits were generated and analyzed by PCR, Southern blot and FISH. One line (3358) did not contain a complete copy of the transgene. The remaining nine lines were all bred to obtain milk for expression analysis.

Example 3

Analysis OF C1 Inhibitor in the Milk of Transgenic Animals

A, B. Overlapping and single genomic constructs in mice (CINH1 and CINH2).

Milk from transgenic mice and non-transgenic controls was analyzed by an enzyme-linked-radio-immuno-assay (for a description of the ELISA, see Appendix 2; for the expression data see Tables 1, 2 and 3). The ELISA measures the total amounts of C1 inhibitor (both active and inactive). The average levels of C1 inhibitor obtained in the transgenic mice made with the overlapping fragments ranged from 0.04–5 mg/ml. Some individual samples of the highest producing lines contained more than 20 mg/ml. The average levels of C1 inhibitor obtained in the transgenic mice made with the single fragment ranged from 0.1 μg/ml–10 mg/ml. Some individual samples of the highest producing line (5903) contained more than 20 mg/ml.

TABLE 1

C1 inhibitor expression data of rH-C1INH1 mouse lines

| Line no | # integration sites | subline | C1 inhibitor expression F1 μg/ml[1] Average[2] | Max[3] |
|---|---|---|---|---|
| 5394 | 1 | | 6 | 17 |
| 5395 | 1 | | 7282 | 10830 |
| 5396 | 1 | | 803 | 1290 |
| 5398 | 1 | | 39 | 123 |
| 5399 | 2 | A | 28 | 46 |
| | | B | 131 | 411 |
| 5400 | 1 | | 9838 | 21902 |
| 5401 | 1 | | 12 | 30 |
| 5402 | 1 | | 855 | 2739 |
| 5403 | 1 | | <1 | <1 |
| 5404 | 1 | | 505 | 1632 |
| 5405 | 2 | A | 2 | 5 |
| | | B | 1 | 2 |
| 5406 | 2 | A | 2768 | 6500 |
| | | B | 2478 | 3236 |
| 5408 | 1 | | 32 | 73 |
| 5410 | 2 | A | 52 | 136 |
| | | B | 3344 | 4345 |
| | | double int. | 3344 | 5099 |

[1]Expression levels were determined by ELISA (Appendix 2A).
[2]Average expression of milk samples from day 6, 9 and 12 post-partum of two lactation periods from all F1 mice of a particular line.
[3]The highest expression found within the milk samples from all F1 mice of a particular line.

TABLE 2

C1 inhibitor expression data of rH-C1INH2 mouse lines

| Line no[1] | C1 inhibitor expression F1 μg/ml[2] | |
|---|---|---|
| | average[3] | max[4] |
| 5895 | 485 | 902 |
| 5896 | 1617 | 5749 |
| 5897 | 0.2 | 0.3 |
| 5898 | 0.1 | 0.1 |
| 5899 | 0.1 | 0.2 |
| 5900 | 91 | 264 |
| 5902 | 0.4 | 1 |
| 5903 | 9721 | 24516 |
| 5904 | 46 | 151 |
| 5905 | 32 | 149 |
| 5906 | 1.3 | 3 |
| 5907 | 62 | 257 |

[1]All lines contained a single transgene integration site, due to pre-selection by FISH.
[2]Expression levels were determined by ELISA (Appendix 2A).
[3]Average expression of milk samples from day 6, 9 and 12 post-partum of two lactation periods from all F1 mice of a particular line.
[4]The highest expression found within the milk samples from all F1 mice of a particular line.

TABLE 3

Summary of the expression data of rH-C1INH1 and rH-C1INH2 mouse lines

| | number of lines expressing (%)[1] | | |
|---|---|---|---|
| Construct | > 1 mg/ml | 0.1 >< 1 mg/ml | < 0.1 mg/ml |
| C1INH1 | 6/19 (31.6) | 4/19 (21.0) | 9/19 (47.4) |
| C1INH2 | 2/12 (16.7) | 2/12 (16.7) | 8/12 (66.7) |

[1]Number of lines divided by the total number of lines

C. Single Genomic Construct in Rabbits.

Milk from transgenic rabbits and non-transgenic controls was analyzed by two different assays (for a description of these ELISAs, see Appendix 2B; for the expression data see Table 4). The ELISA assesses the total amount of antigenic C1 inhibitor protein present in the milk, whereas the C1 inhibitor activity assay measures the amount of functionally active C1 inhibitor. The average levels of active C1 inhibitor obtained in the transgenic rabbits ranged from 0.05–20 mg/ml. Some individual samples of the highest producing lines contained more than 25 mg/ml.

TABLE 4 rH-C1INH rabbit founders: transgene copy numbers and expression levels (protein content and activity).

| Line # | Animal # | Sex | G[1] | # Int. Sites[2] | Chrom. Arm.[2] | Copy #[3] | Expression (g/l)[4] | | | Activity (g/l)[5] | |
|---|---|---|---|---|---|---|---|---|---|---|---|
| | | | | | | | L1 | L2 | L3 | L1 | L2 |
| 1775 | 1775 | M | F0 | 1 | | 4.5 | NA | NA | NA | NA | NA |
| | 3459 | F | F1 | 1 | | 4.5 | 2.1 (9) | | | 2.4 (2) | |
| | 3461 | F | F1 | 1 | | 4.5 | 2.5 (13) | 1.9 (9) | | 2.1 (3) | |
| | 3321 | F | F1 | | | | 2.0 (16) | 1.8 (14) | 1.3 (1) | 1.9 (4) | 1.7 (3) |
| | 3334 | F | F1 | | | | 2.3 (12) | 1.6 (6) | 2.2 (1) | 1.9 (3) | |
| | 3493 | F | F1 | | | | 1.9 (13) | 1.8 (12) | | 1.5 (3) | |
| 2069 | 2069 | F | F0 | 1 | | ? | 0.025 | | | | |
| 2972 | 2972 | M | F0 | 2 | p + q | ? | NA | NA | NA | NA | NA |
| | 3632 | M | F1 | 1 | p | 6.0[6] | | | | | |
| | 3677 | F | F1 | 1 | p | | 12.6 (13) | 13.9 (16) | 12.4 (6) | 16.3 (9) | |
| | 3804 | F | F1 | 1 | p | | 20.3 (2) | | | | |
| | 3806 | F | F1 | 1 | p | | 13.6 (14) | 13.9 (9) | | | |
| | 4461 | F | F2 | 1 | p | | 18.2 (8) | | | | |
| | 3679 | F | F1 | 1 | q | | 6.5 (14) | 6.5 (17) | 7.5 (15) | 5.4 (9) | |
| | 4038 | F | F1 | 2 | ? | | 7.8 (5) | | | | |
| | 3586 | M | F1 | 1 | q | 8.0 | | | | | |
| | 3674 | F | F1 | 1 | q | 8.0 | | | | | |
| | 3676 | F | F1 | 2 | p + q | | 18.8 (13) | 17.6 (7) | | 21.9 (9) | |
| | 3735 | F | F1 | 2 | p + q | | 16.2 (6) | 17.2 (4) | | | |
| | 4042 | F | F1 | 2 | p + q | | 17.3 (9) | | | | |
| 2977 | 2977 | M | | 2 | p + q | 16 + ? | NA | NA | NA | NA | NA |
| | 3748 | F | F1 | 1 | p | | 0.5 (3) | | | | |
| | 3773 | F | F1 | 1 | p | | 1.2 (10) | | | | |
| | 3778 | F | F1 | 1 | q | 16 | 15.7 (12) | 18.6 (9) | | | |
| | 3597 | F | F1 | 2 | p + q | | 12.7 (14) | 13.2 (7) | | 13.9 (9) | |
| 3023 | 3023 | M | F0 | 1 | | 3 | NA | NA | NA | NA | NA |
| | 3640 | F | F1 | | | | 0.45 (8) | | | | |
| | 3802 | F | F1 | 1 | | 3 | 0.215 | | | | |
| | 3659 | F | F1 | | | | 0.26 (7) | | | | |
| 3024 | 3024 | M | F0 | 1 | | 3 | NA | NA | NA | NA | NA |
| | 3802 | F | | | | | 0.28 (3) | | | | |
| | 3824 | F | F1 | 1 | | 4.5 | 0.72 (3) | | | | |
| | 3832 | F | F1 | | | | 0.34 (2) | | | | |
| | 3836 | F | F1 | | | | 0.14 (2) | | | | |
| | 3951 | F | F1 | | | | 0.68 (1) | | | | |
| | 3958 | F | F1 | | | | 0.24 (1) | | | | |
| 3368 | 3368 | F | F0 | 1 | | 7 | 1.2 (19) | 1 (17) | | 1.2 (9) | 0.65 (2) |
| 3370 | 3370 | M | F0 | 1 | | 8 | NA | NA | NA | NA | NA |

TABLE 4-continued rH-C1INH rabbit founders: transgene copy numbers and expression levels (protein content and activity).

| Line # | Animal # | Sex | G[1] | # Int. Sites[2] | Chrom. Arm.[2] | Copy #[3] | Expression (g/l)[4] | | | Activity (g/l)[5] | |
|---|---|---|---|---|---|---|---|---|---|---|---|
| | | | | | | | L1 | L2 | L3 | L1 | L2 |
| 3376 | 3376 | M | F0 | 1 | | 5.5 | NA | NA | NA | NA | NA |
| | 4253 | F | F1 | | | | 13.2 (13) | | | | |
| 3558 | 3558 | F | F0 | 1 | | 0.5[7] | | | | | |

[1] = generation
[2] = determined by metaphase FISH
[3] = determined by FiberFISH
[4] = concentration of C1 inhibitor antigen (Appendix 2B I); average of (n) samples
[5] = concentration of functionally active C1 inhibitor (Appendix 2B II); average of (n) samples
[6] = six complete + two half copies present
[7] = no complete copy present

Example 4

Purification of Recombinant Human C1INH from Rabbit Milk

The presence of R-C1INH in milk was confirmed by immunoblotting and SDS-PAGE analysis of fractions that were obtained after purification from non-transgenic rabbit milk. From the estimated level of R-C1INH and the concentration of rH-C1INH in transgenic milk it was concluded that separation was necessary. Separation of rH-C1INH from R-C1INH was achieved using anion exchange chromatography on Q Sepharose (Pharmacia) at pH 5.5 and 7.0. The difference in elution was about 0.1 M sodium chloride, which is suitable enough for manufacturing.

Transgenic rabbit milk from line 2972p having a rH-C1INH concentration of 15 g/l was thawed, pooled and diluted with 1 volume of 20 mM sodium citrate pH 5.5. The pH after dilution was 7.0. The diluted milk was subsequently filtered over a 25 µm Polygard® filter (Millipore) and skimmed by continues centrifuigation at room temperature. Two hundred milliliter of the skimmed milk was applied on a SP Sepharose big beads (Pharmacia) column (50/15) that was equilibrated in 20 mM sodium citrate pH 7.0+0.05 M sodium chloride. The linear flow was 60 cm/h. After loading the column was washed with 5 column volumes of 20 mM sodium citrate pH 7.0±0.05 M sodium chloride and bound rH-C1INH was eluted with a step of 20 mM sodium citrate pH 7.0+0.2 M sodium chloride. The eluted rH-C1INH was filtered through 0.22 µm, 3 fold diluted in 20 mM sodium phosphate pH 7.0 and applied with a linear flow of 60 cm/h on a Q Sepharose high performance (Pharmacia) column (50/20), equilibrated in 20 mM sodium phosphate pH 7.0+0.05 M sodium chloride. After washing the column with 10 volumes of 20 mM sodium phosphate pH 7.0+0.05 M sodium chloride at a linear flow of 90 cm/h bound rH-C1INH was eluted with a step of 20 mM sodium phosphate pH 7.0+0.25 M sodium chloride. The linear flow during elution was 60 cm/h. The rH-C1INH fraction was subsequently loaded on a Zinc charged Chelating Sepharose fast flow (Pharmacia) column (50/15) with a linear flow of 60 cm/h in 20 mM sodium phosphate pH 7.0+0.25 M sodium chloride. The protein fraction that was not absorbed by the column was concentrated and buffer exchanged to phosphate buffered saline using a 50 cm2 Biomax-30 membrane (Millipore). The concentrated rH-C1INH was filtered through 0.22 µm, aliquot and stored below −70° C.

The recovery of this process was monitored using a specific ELISA for rH-C1INH and was around 40%. In addition the activity of rH-C1INH throughout the purification was preserved as determined by the inhibition of C1s. The purity was determined above 99% by SD S-PAGE and size exclusion chromatography and above 99.95% using a specific ELISA that detects host proteins present in rabbit milk.

Determining the Purity of RH-C1INH Preparations

Size Exclusion Chromatography

Purified rH-C1INH (100 µl, 2 mg/ml) was filtered through a Superose 12 HR 10/30 gel filtration column (Pharmacia) in phosphate buffered saline +0.15 M sodium chloride with a flow of 0.5 ml/min (Äka explorer 10 system, Pharmacia). Eluting protein was detected by absorption at 205 nm. The percentage of eluting peaks was determined by integration using the Unicom software (Pharmacia).

Host Related Impurity Detection

The relative presence of host-related impurities (HRI) in the final product was determined by a quantitative enzyme immunoassay (ELISA). Polyclonal antibodies binding to human C1 inhibitor without binding to rabbit C1 inhibitor were generating by immunizing rabbits with human C1 inhibitor. Specific antibodies against rabbit milk proteins were generated by immunization of sheep and goats with milk and whey proteins. The specificity of the antisera was evaluated by Western blot analysis. Those antisera that reacted with most if not all rabbit milk proteins were selected. The total IgG-fraction was purified on Protein G Sepharose according to the manufacturer instructions (Pharmacia). The purified IgG was used for the development of the sandwich ELISA.

Microtitre plates (Polysorp, Nunc) were coated overnight at room temperature with 5 µg/ml purified IgG in 0.1 M sodium carbonate pH 9.4. After washing with PBS/0.02% Tween-20, the wells were incubated with samples diluted in PBS/0.3% BSA/0.1% Tween-20/10 mM EDTA for 1 hour at room temperature. After washing with PBS/0.02% Tween-20 wells were incubated with peroxidase labeled IgG (1:2000 in PBS/0.3% BSA/0.1% Tween-20) for 1 hour at room temperature. After another wash, substrate solution (ImmunoPure TMB Substrate Kit, Pierce) was added. Substrate conversion was stopped by the addition of 2 M H2SO4 and plates were read at 450 nm in SLT 340 ATTC plate reader (SLT Labinstruments) using BIOLISE software. All incubations were performed with 100 µl volumes.

The total amount of host related impurities, expressed as parts per million (PPM) on a weight to weight basis, was calculated from the reactivity of purified rH-C1INH samples compared to a milk standard of which the total protein concentration was determined by the Bicinchonic assay (Pierce) using bovine serum albumin as standard.

For control purpose, rabbit C1 inhibitor was purified from rabbit plasma. The purification was effected by precipitation with polyethylene glycol, capturing by cation exchange chromatography, intermediate purification by lectin affinity chromatography, and polishing by anion exchange chromatography.

Example 5

Purification of Recombinant C1 Inhibitor from Milk of Different Transgenic Rabbit Founders Milk pools from lines 2972q, 2972p and 2977q were mixed with equal volumes of 20 mM sodium citrate pH 5.5 where after pH was adjusted to 7.0. The diluted milk was defatted by centrifugation at 1300 g for 20 minutes at 4 C and subsequently subjected to cation exchange chromatography on a SP Sepharose column equilibrated in 20 mM sodium citrate pH 7.0 (buffer A). After loading, the column was washed with buffer A and bound proteins were eluted with 0.15 M sodium chloride in buffer A at a linear flow rate of 60 cm/h. Eluting fractions containing C1 inhibitor, as determined with the specific ELISA (see Appendix 2BI), were pooled and micro-filtered (0.45 μm), followed by filtration through a Superdex 200 gelfiltration column (in 20 mM sodium phosphate, containing 0.15 M NaCl at a linear flow of 15 cm/h). C1 inhibitor containing fractions were pooled, aliquoted and stored below −50 C. The recovery of each step was determined to be above 90%. The purity, as determined using quantitative SDS-PAGE (see Appendix 3), was above 98%.

Cetor® (=C1 inhibitor purified from pooled human plasma, CLB, The Netherlands) used as control in characterization studies was also filtered on Superdex 200 under the same conditions as mentioned above.

Example 6

Characterization of the Different Recombinant C1 Inhibitor Preparations

Functionality Index

The functionality index (F.I.), defined as the ratio between functionally active C1 inhibitor and total C1 inhibitor antigen, is given in Table 5. The amount of total C1 inhibitor antigen is measured using an ELISA as described in Appendix 2BI. The amount of functionally active C1INH is determined using the C1INH activity test, as described in Appendix 2BII.

TABLE 5

The functionality index (F.I.) of the different C1INH preparations

| C1INH-preparation | Total C1INH antigen (mg/ml) | functionally active C1INH (mg/ml) | F.I. |
|---|---|---|---|
| Cetor ® | 0.86 | 0.92 | 1.07 |
| 2972 p | 1.56 | 1.79 | 1.15 |
| 2972 q | 1.69 | 1.80 | 1.07 |
| 2977 q | 2.04 | 1.85 | 0.91 |

SDS-PAGE and Western-blot Analyses

The different C1 inhibitor preparations were analyzed on 4–20% SDS-PAGE under reducing and non-reducing conditions. All C1 inhibitor preparations migrate as a single band under both reducing and non-reducing conditions and the bands are recognized by rabbit anti-C1 inhibitor antibodies (DAKO, A0253) on Western blot.

Under non-reducing conditions Cetor® has an apparent molecular weight of approximately 105 kDa, whereas the three different recombinant C1 inhibitor all have an apparent molecular weight of approximately 96 kDa. Under reducing conditions the apparent molecular weights are approximately 95 kDa for Cetor® and 80 kDa for the recombinant C1INH preparations.

C-terminal Sequence Analyses

The sequence analysis was performed by C-terminal degradation (Boyd V L et al. (1992) Anal. Biochem. 206, 344–352; Boyd V L et al. (1995) J. Organic Chem. 60, 2581–2587) with an automated sequenator (Model 477A, Applied Biosystems) using protocols, reagents, chemicals and materials from Applied Biosystems (Warrington, UK and Foster City, Calif., USA). Step-wise released ATH-amino acids were identified with an on-line HPLC (Model 120A, Applied Biosystems) on the basis of their elution times.

Identical C-terminal sequence were found in the different recombinant C1 inhibitor preparations and Cetor®. In each sample, the main sequence showed an Ala at the C-terminus. Due to the limitations of the analysis method, amino acids could not be determined at position 2 to 4 (starting from the C-terminus). Analysis of the minor signals reveals that there is no apparent C-terminal heterogeneity in the different recombinant C1 inhibitor preparations and Cetor®.

Example 7

Purification of Recombinant Human C1INH at 10 Liter Milk Scale

Frozen milk from line 2972p, 11 kg in total, was stored frozen, thawed and pooled. After thawing an equal amount of 20 mM sodium citrate pH 5.5 was added. The diluted milk was filtered over 25 μm and skimmed by continues centrifugation at room temperature. The skimmed milk was subsequently applied with a flow of 60 cm/h on a SP Sepharose big bead (Pharmacia, Sweden) column (450/15) that was equilibrated in 20 mM sodium citrate pH 7.0+0.02 M sodium chloride. After loading, the column was washed with 5 column volumes of 20 mM sodium citrate pH 7.0+0.02 M sodium chloride and bound rH-C1INH was eluted with a step of 20 mM sodium citrate pH 7.0+0.2 M sodium chloride. The eluted rH-C1INH was filtered through 0.2 pm and incubated for 6 hours at 25° C. in the presence of 1% Tween 80 (Merck, Germany) and 0.3% Tri (n) Butyl Phosphate (Merck, Germany) to inactivate enveloped viruses. After viral inactivation the pool was 3-fold diluted in 20 mM sodium phosphate pH 7.0, filtered over 0.2 μm and applied with a flow of 60 cm/h on a Q Sepharose high performance (Pharmacia, Sweden) column (450/15) that was equilibrated in 20 mM sodium phosphate pH 7.0+0.05 M sodium chloride. After washing of the column with 5 column volumes of 20 mM sodium phosphate pH 7.0+0.05 M sodium chloride, bound rH-C1INH was eluted with a step of 20 mM sodium phosphate pH 7.0+0.22 M sodium chloride. The Q Sepharose eluate was subsequently 2-fold diluted in 20 mM sodium phosphate pH 7.0, 0.2 μm filtered and applied with a flow of 30 cm/h on a zinc charged Chelating Sepharose fast flow (Pharmacia, Sweden) column (450/15), equilibrated in 20 mM sodium phosphate pH 7.0+0.1 M sodium chloride. After loading, the column was washed with 20 mM sodium phosphate pH 7.0+0.1 M NaCl and the protein fraction that had not been absorbed by the column was collected. This protein fraction was further filtered over 0.2 µm followed by filtration over a Vira/Gard 500 membrane (AG/T, USA) for removal of possible viral contaminants. In a later experiment a Planova 15N filter from Asahi (Japan) replaced the Vira/Gard membrane. After this viral filtration, the rH-C1INH was concentrated and buffer exchanged to 20 mM sodium citrate pH 7.0 using a Biomax-10 membrane (Millipore, USA). The concentrated rH-C1INH was filtered through 0.1 µm, vialed and stored at −20° C. In a later experiment 6.5% sucrose was added to the concentrated rH-C1INH, which was subsequently filtered through 0.1 µm, vialed and freeze-dried.

The recovery of this process was 37% using a specific ELISA for rH-C1INH. In addition the activity of rH-C1INH throughout the purification was preserved as determined by the inhibition of C1s. The purity was determined above 99% by size exclusion chromatography and above 99.999% using a specific ELISA that detects host proteins present in rabbit milk. The amount of endogenous R-C1INH was quantitated below 1 ppm.

(3,3',5,5' tetramethylbenzidin) staining reaction. Color development was stopped after 20 minutes with 100 µl/well 2 M $H_2SO_4$ and read at 450 nm with a 340 ATTC plate reader (SLT Labinstruments), using BIOLISE software (version 1.65). All incubations were performed at room temperature (1 hour) and between every incubation, the wells were washed 5 times with phosphate buffered saline (PBS) containing 0.02% Tween-20. Serial dilutions of pooled normal human plasma (NP) were used as a reference to calculate C1 inhibitor levels in milk. According to CLB standards, NP contains 275 µg/ml C1 inhibitor.

B. Description of the Methods used to Determine the Functional and Antigenic C1 Inhibitor Levels in Transgenic Rabbit Milk I. Determination of Total C1 Inhibitor Antigen Levels 96 wells ELISA plates were coated with 3.5 µg/ml rabbit anti-C1 inhibitor antibodies (DAKO, A0253) in phosphate buffered saline, pH 7.4 (PBS) (100 µl/well) overnight at room temperature. After washing, the wells were incubated with 100 µl/well diluted milk samples for 1 hour at room temperature. Bound C1 inhibitor was detected using 100 µl/well 1:5000 diluted peroxidase labeled rabbit anti-C1 inhibitor antibodies (1 hour at room temperature) and visualized with 100 µl/well 3,3',5,5' teramethylbenzidin (=TMB, ImmunoPure TMB Substrate Kit, Pierce 34021) as a sub-

```
A.
Forward primer:  5'-TCTCTCAGATCTTCCACAGCC-3'
                 (SEQ ID NO:1)
Reverse primer:  5'-AAGGTCTTCACCTGCTCTGC-3'
                 (SEQ ID NO:2)

B.                     EcoRI         NotI
Linker 1         5'-TCGA CGAATTCGGCCCCCGGGGCCGCGGCCGCA-3'
                 (SEQ ID NO:3)
                 3'-GCTTAAGCCGGGGGCCCCGGCGCCGGCGT TTAA-5'
                 (SEQ ID NO:4)

C.                       ClaI  αS1 casein exon 1        NcoI   MluI
Linker 2         5'-GGCC GCATCGATTTGCTTCTTTCCAGTCTTGGCCCAGATGGCCCCATGGACGCG-3'
                 (SEQ ID NO:5)
                 3'-CGTAGCTAAACGAAGGTCAGAACCGGGTCTACCGGGGTACCTGCGC AGCT-5'
                 (SEQ ID NO:6)

D.                       BglI       NotI
Linker 3         5'-TGGCCGACGGCCAACATGGCCGCGGCCGCGATATCA-3'
                 (SEQ ID NO:7)
                 3' TCT ACCGGCTGCCGGTTGTACCGGCGCCGGCGCTATAGTGCGC-5'
                 (SEQ ID NO:8)

E.                      NotI
Linker 4         5'-CTAG TGCGGCCGCTGATCAG-3'
                 (SEQ ID NO:9)
                 3'-ACGCCGGCGACTAGTC AGCT-5'
                 (SEQ ID NO:10)
```

Appendix 2

A. Description of the Method used to Determine the Total Amount of Antigenic C1 Inhibitor in Transgenic Mouse Milk The C1 inhibitor expression levels in mouse milk were determined using an ELISA according to Veerhuis et al. (1998) [Veerhuis. 1998 Acta Neuropathol 96, 287–296]. In short. 96-well ELISA plates were coated with monoclonal anti-C1 inhibitor antibodies, followed by an incubation with milk samples. Bound C1 inhibitor was detected using biotinylated rabbit anti-C1 inhibitor antibody followed by an incubation with peroxidase labeled streptavidine and a TMB strate. Colour development was stopped after 20 minutes with 100 µl/well 2 M $H_2SO_4$ and read at 450 nm with a 340 ATTC plate reader (SLT Labinstruments), using BIOLISE software (version 1.65). Results were calculated by reference to serial dilutions of C1 inhibitor purified from plasma (Sigma, E0518) (0–130 ng/ml). All dilutions of (milk) samples and conjugate were prepared in PBS/2% milk/0.1% Tween-20.

II. C1 Inhibitor Activity

25 µl diluted milk samples were incubated with 25 µl 1.5 µg/ml C1s (Kordia, The Netherlands/Enzyme Research Lab. Inc., USA) in wells of a 96 wells plate, for 60 minutes at room temperature. Afterwards, the remaining C1s activity was determined by adding 25 µl 1 mM Pefachrome® C1E-5019 (Kordia, The Netherlands/Pentapharm Ltd., Switzerland, PF 087-31). Immediately after addition of the chromogenic substrate the change in absorbance at 450 nm was monitored for 45 minutes at 37° C. using a 340 ATTC plate reader (SLT Labinstruments), using BIOLISE software (version 1.65). Results were related to a calibration curve prepared by serial dilutions of plasma purified C1 inhibitor (Sigma, E0518) (0–6 µg/ml). Milk samples and C1s were diluted in PBS/0.1% Tween-20. Pefachrome® C1E-5019 was diluted in distilled water.

Appendix 3

Quantitative SDS-PAGE to Determine the Purity of the Different C1 Inhibitor Preparations.

C1 inhibitor obtained from Sigma (Sigma, E0518) and the different purified recombinant C1 inhibitor preparations were diluted in PBS/0.1% Tween-20 and mixed with an equal volume of non-reduced sample buffer (Tris-glycin (pH 6.8) Novex, LC2676). The concentrations of the calibration samples varied between 1 µg/ml and 25 ng/ml and the purified recombinant C1 inhibitor preparations had a concentration of 500 µg/ml. 10 µl of each sample was applied to 4–20% SDS-PAGE (Tris-glycin, Novex, EC60252) and the gels were run and silver stained according to standard procedures. The intensity of the various individual bands on gel was measured using a Fluor-S™ MultiImager (BIO-RAD). The intensity of the different calibration samples was plotted against the amount of protein loaded on the gel and the best curve was fitted through the points. The amount of impurity (ng) in the different C1 inhibitor preparations was calculated using the calibration curve. The percentage of impurity of a sample is the relative amount of total impurities compared to the total amount of protein loaded on the gel.

The invention claimed is:

1. A nonhuman mammal whose genome comprises a DNA segment encoding a C1 inhibitor heterologous to the mammal operably linked to at least one expression regulatory sequence from a gene that is preferentially expressed in mammary gland cells and a DNA segment encoding a signal peptide functional in mammary gland cells; wherein the DNA segment encoding the C1 inhibitor can be expressed in the mammary gland cells to produce C1 inhibitor in the milk of an adult form of said mammal or a female descendant thereof.

2. The nonhuman mammal of claim 1, wherein the concentration of the C1 inhibitor in the milk is at least 1 mg/ml.

3. The nonhuman mammal of claim 1, wherein the C1 inhibitor is human.

4. The nonhuman mammal of claim 1, that is a mouse, rabbit, goat, sheep, porcine or bovine.

5. The nonhuman mammal of claim 4, wherein the DNA segment is cDNA.

6. The nonhuman mammal of claim 4, wherein the DNA segment is genomic.

7. The nonhuman mammal of claim 4, wherein the DNA segment is a cDNA-genomic hybrid.

8. The nonhuman mammal of claim 1, wherein the signal peptide is a C1 inhibitor signal peptide.

9. A method for providing C1 inhibitor comprising: recovering milk from the adult form of the transgenic nonhuman mammal or its female descendant of claim 1.

10. The method of claim 9, further comprising purifying the C1 inhibitor from the milk.

11. The method of claim 10, wherein the C1 inhibitor is at least 95% pure.

12. The method of claim 11, further comprising mixing the C1 inhibitor with a carrier.

13. Milk from a nonhuman transgenic mammal whose genome comprises a DNA segment encoding a C1 inhibitor heterologous to the mammal operably linked to at least one expression regulatory sequence from a gene that is preferentially expressed in mammary gland cells and a DNA segment encoding a signal peptide functional in mammary gland cells; wherein the DNA segment encoding the C1 inhibitor can be expressed in the mammary gland cells to produce C1 inhibitor in the milk of an adult form of said mammal or a female descendant thereof.

14. The milk of claim 13, wherein the concentration of C1 inhibitor protein is at least 1 mg/ml.

15. The milk of claim 14, wherein the C1 inhibitor has a functionality index of at least 0.9.

16. The method of claim 10, where the purifying comprises: loading the milk onto a cationic exchange column under conditions in which the human C1 inhibitor binds to the column; eluting the human C1 inhibitor from the cationic exchange column; loading the eluate on an anionic exchange column under conditions in which the human C1 inhibitor binds to the column; eluting the human C1 inhibitor from the anionic exchange column; loading the eluate onto a metal ion exchange column under conditions in which residual contaminating proteins bind to the column; collecting eluate containing the human C1 inhibitor from the metal ion exchange column.

17. The method of claim 16, wherein the sample further comprises rabbit C1 inhibitor; and the eluate from the metal ion exchange column has a higher ratio of human C1 inhibitor to rabbit C1 inhibitor than the sample.

18. The method of claim 17, wherein the ratio is at least 500:1.

* * * * *